United States Patent
Meessen

(10) Patent No.: US 9,346,016 B2
(45) Date of Patent: May 24, 2016

(54) PROCESS FOR THE PREPARATION OF A UREA-COMPRISING AQUEOUS STREAM

(71) Applicant: Jozef Hubert Meessen, Wijlre (NL)

(72) Inventor: Jozef Hubert Meessen, Wijlre (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 13/754,584

(22) Filed: Jan. 30, 2013

(65) Prior Publication Data

US 2013/0207035 A1 Aug. 15, 2013

Related U.S. Application Data

(63) Continuation of application No. 11/885,666, filed as application No. PCT/NL2006/000097 on Feb. 24, 2006, now abandoned.

(30) Foreign Application Priority Data

Mar. 9, 2005 (NL) ...................................... 1028497

(51) Int. Cl.
*C07C 273/02* (2006.01)
*C07C 273/16* (2006.01)
*B01D 53/92* (2006.01)
*B01D 53/79* (2006.01)
*B01D 53/90* (2006.01)

(52) U.S. Cl.
CPC ............... *B01D 53/92* (2013.01); *B01D 53/79* (2013.01); *B01D 53/90* (2013.01); *C07C 273/16* (2013.01); *Y02C 20/10* (2013.01)

(58) Field of Classification Search
USPC .............. 60/295; 423/213.2, 239.1, 355, 356, 423/365; 71/28; 564/1
See application file for complete search history.

(56) References Cited

U.S. PATENT DOCUMENTS

| | | | |
|---|---|---|---|
| 6,361,754 | B1 | 3/2002 | Peter-Hoblyn et al. |
| 2003/0033799 | A1 | 2/2003 | Scheying |
| 2003/0118494 | A1 | 6/2003 | Glesmann et al. |
| 2003/0135072 | A1 | 7/2003 | Scholten et al. |
| 2004/0098978 | A1 | 5/2004 | Tarabulski et al. |
| 2004/0116743 | A1 | 6/2004 | Mennen |

FOREIGN PATENT DOCUMENTS

| | | |
|---|---|---|
| EP | 0 266 840 | 5/1988 |
| EP | 0 934 927 | 8/1999 |
| EP | 1 203 765 | 5/2002 |
| EP | 1 283 332 A2 | 6/2002 |
| EP | 1 388 648 | 2/2004 |

(Continued)

OTHER PUBLICATIONS

Patent Abstracts of Japan, vol. 2003, No. 12, Dec. 5, 2003 & JP 2004-156471, Jun. 3, 2004.

(Continued)

*Primary Examiner* — Stuart Hendrickson
*Assistant Examiner* — Daniel Berns
(74) *Attorney, Agent, or Firm* — Nixon & Vanderhye P.C.

(57) ABSTRACT

The invention relates to process for the preparation of a urea-comprising aqueous stream, that is suitable for use in a unit for the reduction of NOx in combustion engine exhaust gases, wherein the urea-comprising aqueous stream is separated directly from or after a recovery section in a urea production process and is thereafter diluted with water until the urea-comprising stream comprises 30-35 wt % urea.

8 Claims, 2 Drawing Sheets

(56) References Cited

FOREIGN PATENT DOCUMENTS

| | | |
|---|---|---|
| GB | 913422 | 12/1962 |
| JP | 6-329614 | 11/1994 |
| JP | 2005-814 | 1/2005 |
| WO | 96/23767 | 8/1996 |
| WO | 00/21881 | 4/2000 |
| WO | 01/51429 A2 | 7/2001 |
| WO | 01/51429 A3 | 7/2001 |

OTHER PUBLICATIONS

International Search Report mailed May 3, 2006 in PCT/NL2006000097.
Japanese Office Action dated Mar. 6, 2012. (Regarding Appl 'n No. P2008-500647).
Notice of Opposition to a European Patent, EP Patent No. 1856038, Urea Casale SA, Sep. 14, 2011, pp. 1-5.
Notice of Opposition to a European Patent, EP Patent No. 1856038, Yara International ASA, Sep. 14, 2011 pp. 1-6.
Kirk-Othmer, "Encyclopedia of chemical technology, vol. 23", John Wiley & Sons, 1983, ED. $3^{rd}$ (D01).
"Ullmann's Encyclopedia of Industrial Chemistry", vol. A27, 1996, Ed. $5^{th}$ (D02).
"Urea synthesis: a status report—I", Nitrogen, vol. 185, May 1990 (D03).
Priority Document, NL1028497, Mar. 5, 2005 (D15).
Integer Research, "SCR and AdBlue: Key Issues and Prospects", Diesel SCR and AdBlue, Feb. 2005 (D16).
Yara, "New exhaust emission standard for heavy-duty vehicles from 2005", Press release Yare, Jan. 13, 2005 (D6).
Hydro, "News from Hydro", Press release Hydro, Dec. 2, 2003 (D7).
European Fertilizer Manufacturers' Association (EFMA), "Best Available Techniques for Pollution Prevention and Control in the European Fertilizer Industry", Production of Urea and Urea Ammonium Nitrate, 2000 (D9).
Lee et al, "Solubility of Urea in Water-Alcohol Mixtures," J. Chem. & Eng. Data, vol. 17, No. 3, 1972, pp. 304-306.

PROCESS FOR THE PREPARATION OF A UREA-COMPRISING AQUEOUS STREAM

CROSS-REFERENCE TO RELATED APPLICATIONS

This application is a continuation of commonly owned U.S. Ser. No. 11/885,666, filed Sep. 5, 2007, which is the national phase application under 35 USC §371 PCT/NL2006/000097, filed Feb. 24, 2006 which designated the US and claims benefit of NL 1028497, filed Mar. 9, 2005, the entire contents of each of which are hereby incorporated by reference.

FIELD

The invention relates to a process for the preparation of a urea-comprising aqueous stream which is suitable for use in a unit for the reduction of $NO_x$ in combustion engine exhaust gases.

BACKGROUND AND SUMMARY $NO_x$ emissions from combustion engines (for instance diesel engines) with an exhaust gas catalyst can be reduced by injection of reducing components into the exhaust pipe of these diesel engines before the exhaust gas is contacted with a SCR or an EGR catalyst. The use of a urea-comprising aqueous stream as a reducing agent for this purpose offers special advantages, in particular in diesel engines used to power cars and trucks. The quality requirements to be met by such a urea-comprising aqueous stream are known, for example from DIN Vornorm V70070.

Such a urea-comprising aqueous stream is currently prepared by dissolving commercially available solid urea in clean water while adding heat. The solid urea is available in the form of, for example, urea granulate or urea prills.

A problem encountered is that commercially available solid urea is contaminated with formaldehyde or other additives, because the formaldehyde or the other additives are added to improve the properties of the solid urea and facilitate granulation or prilling of the urea. According to the Vornorm cited above only very low amounts of contaminants are allowed in a urea-comprising aqueous stream that will be used in a unit for the reduction of $NO_x$. A urea-comprising aqueous stream obtained by dissolving solid urea does not meet the quality requirements according to the Vornorm.

At this moment the solid urea or the urea-comprising aqueous stream obtained from it is purified by removing the formaldehyde, the reaction products of formaldehyde and urea and other additives using known separation techniques. However, this process is expensive.

It is the aim of the invention to eliminate these drawbacks.

This is achieved by separating the urea-comprising aqueous stream directly from or after a recovery section in a urea production process and thereafter dilute the urea-comprising aqueous stream with water until the urea-comprising stream comprises 30-35 wt % urea.

In this way a urea-comprising aqueous stream that does not contain formaldehyde, reaction products of formaldehyde and urea or other additives is directly obtained.

A further advantage is that no solid urea needs to be dissolved in water in order to obtain a urea-comprising aqueous stream.

DETAILED DESCRIPTION

Figure 1:
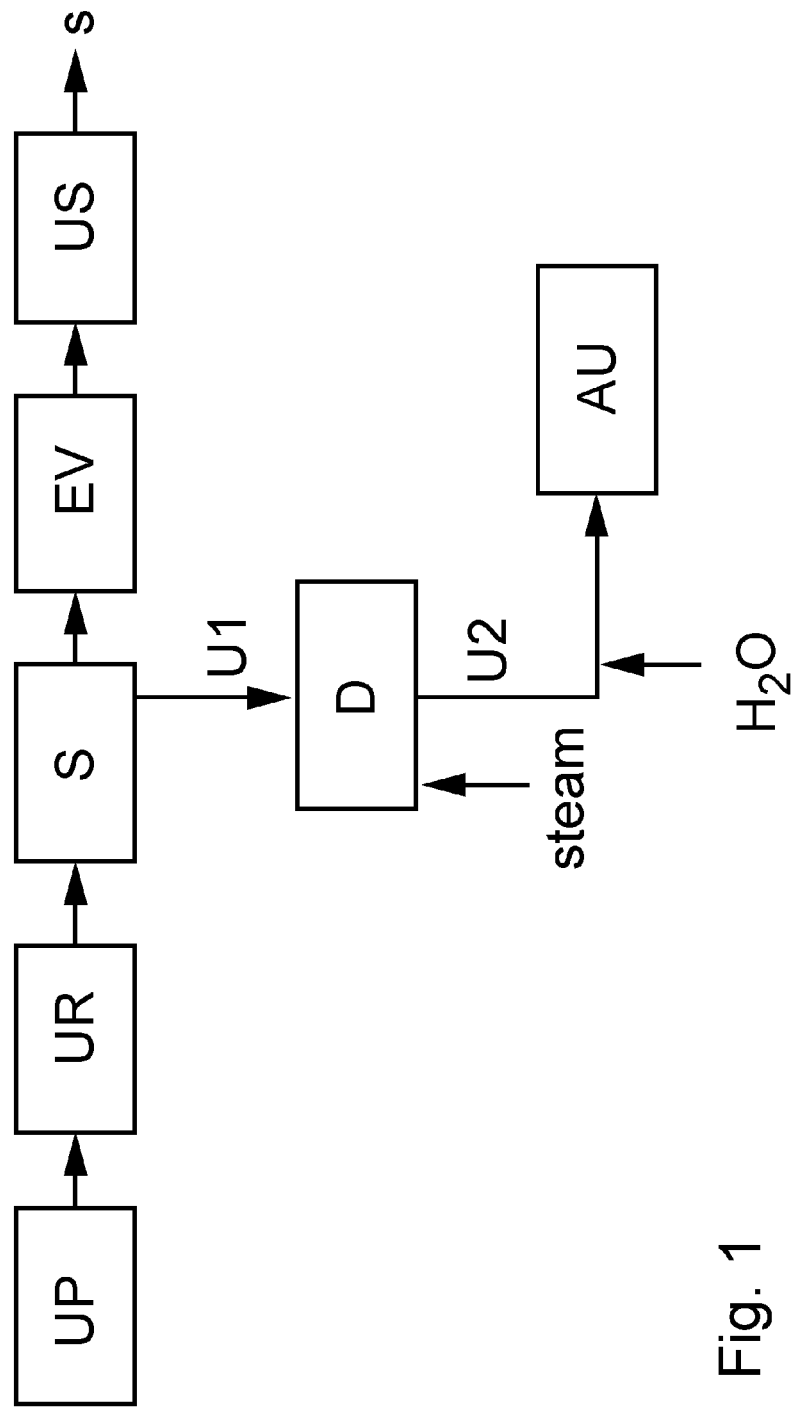
FIG. 1 schematically depicts a urea production process comprised of a urea synthesis section (UP), a urea recovery section (UR), a urea storage tank (S), an evaporation section (EV) and a shaping section (US)

Commercial production of urea usually takes place from $NH_3$ and $CO_2$, according to known processes, such as for example a conventional urea process, a $CO_2$ stripping process, a thermal striping processes and the ACES process. All these processes consist of a urea synthesis section and one or more recovery sections, in which a urea-comprising aqueous stream with a urea content of more than 50 wt % is produced. Subsequently, the urea-comprising aqueous stream is concentrated further, to a water content between 0.1 and 5 wt %, in an evaporation or crystallization section. This water content depends on the requirements set in the shaping section present in the urea production process. Examples of shaping techniques are prilling and granulation. For the benefit of the shaping technique, and also for improvement of the product quality of the solid urea (transport properties), formaldehyde, reaction products of formaldehyde and urea or other additives are added to the urea-comprising aqueous stream during or after the evaporation/crystallization process.

The urea-comprising aqueous stream can be separated from an existing urea process. The urea-comprising aqueous stream can be the total urea-comprising stream resulting from the urea process or it can be a part of it. It is also possible to design a new urea process that is particularly suitable for the production of a urea-comprising aqueous stream that will be used in a unit for the reduction of $NO_x$, in combustion engine exhaust gases. An advantage of the design of a new urea process is that this new process does not need to comprise an evaporation or crystallization section and a shaping section.

The urea-comprising aqueous stream is separated directly from or after a recovery section in the urea production process. The urea-comprising aqueous stream may come from one recovery section but also, if the urea production process comprises more recovery sections, from several recovery sections.

The urea-comprising aqueous stream can be one stream that is separated from one location in the urea production process or it can be composed of several streams that are separated at various locations from the urea production process. After separation the urea-comprising aqueous stream is diluted with water.

In the recovery section(s) of a urea production process the ammonium carbamate, free carbon dioxide and free ammonia content of the urea synthesis solution is reduced. This is done by heating the solution and optionally by reducing the pressure. This temperature increase and optionally also pressure decrease causes the ammonium carbamate that is present to dissociate into free ammonia and free carbon dioxide. A substantial part of this free ammonia and free carbon dioxide passes into the gas phase, which is separated from the rest of the urea-comprising aqueous stream in liquid/gas separators. In the various urea production processes different pressure and temperature levels are applied in the recovery section(s). In some processes a stripping medium is added to one or more dissociation steps in order to promote the dissociation process. Examples of a suitable stripping medium are ammonia gas, carbon dioxide gas, air and steam. The various processes also differ in the way in which the expelled gaseous ammonia and carbon dioxide are processed. While the urea solution flows through the various dissociation steps, the alkalinity and the ammonium carbamate content are reduced.

It is preferred to separate the urea-comprising aqueous stream after a dissociation unit in a urea production process in which at least one of the recovery sections comprises a dissociation unit and in which dissociation is promoted by the addition of a stripping medium.

Preferably, the urea-comprising aqueous stream is separated after the recovery section(s). More preferably, the urea-comprising aqueous stream is separated after the recovery section(s) and before an evaporation section.

In a urea process, wherein a urea storage tank is present after the recovery section(s) and, when a shaping section is present, before the shaping section, the urea-comprising aqueous stream is, more preferably, separated from the urea storage tank.

The urea-comprising aqueous stream that is separated directly from or after a recovery section in a urea production process preferably comprises 60-90 wt % urea.

For use of the urea-comprising aqueous stream in a unit for the reduction of $NO_x$ in combustion engine exhaust gases, the urea-comprising stream that is directly separated from a urea production process needs to be diluted until the urea-comprising stream comprises 30-35 wt % urea.

By separating the urea-comprising aqueous stream from a urea production process in the way according to the invention it is achieved that a urea-comprising aqueous stream is obtained that usually has a sufficiently low alkalinity and carbonate (as $CO_2$ content) to make these solutions suitable to be used in a unit for the reduction of $NO_x$, in combustion engine exhaust gases.

In the rare cases that this is not the case, the alkalinity (as $NH_3$ content) and the carbonate (as $CO_2$ content) of the urea-comprising aqueous stream can simply be reduced further by subjecting the urea-comprising aqueous stream to dissociation before or after dilution with water. Preferably, the dissociation is performed before dilution with water, since then the amount of solution to be subjected to dissociation is limited. In some cases it might however be more favourable to perform the dissociation after the dilution with water, since this would allow for lower temperatures in the dissociation process without formation of solids during dissociation. A reduced temperature is of advantage to minimize the amount of urea lost through hydrolysis, as well as to minimize the amount of biuret formed during dissociation.

The dissociation can be performed, optionally, by the addition of heat and/or with the addition of a suitable stripping medium and/or by reduction of the pressure.

Preferably, the dissociation is performed by steam stripping at a pressure of 0.001-0.2 MPa. The use of steam as a stripping medium prevents the formation of solid material during stripping, which would result in transport problems of the solution. By the use of a reduced pressure during dissociation the temperature during dissociation can be kept low, such that hydrolysis of urea is prevented.

The invention will be elucidated hereinafter on the basis of FIGS. 1 and 2, without being restricted to these embodiments.

FIG. 1 schematically depicts an embodiment of a urea production process comprising a urea synthesis section (UP), a urea recovery section (UR), a urea storage tank (S), an evaporation section (EV) and a shaping section (US). The end product of this urea production process is solid urea (s).

From the urea storage tank (S) a urea-comprising aqueous stream is separated comprising 75 wt % urea. This urea-comprising aqueous stream (U1), having an alkalinity of 0.7% (as $NH_3$) and a carbonate content (as $CO_2$) of 0.7%, enters a dissociation unit (D), wherein the urea-comprising aqueous stream is stripped with steam under a pressure of 0.04 MPa.

After dissociation the urea-comprising aqueous stream is diluted with water to a urea content of 31.5 wt % urea.

A urea-comprising aqueous stream (U2) with a urea content of 31.5 wt %, an alkalinity (as $NH_3$) of 300 ppm and a carbonate content (as $CO_2$) of 300 ppm is stored as a urea-comprising aqueous stream (AU), that is suitable for use in a unit for the reduction of $NO_x$, in combustion engine exhaust gases.

Figure 2:
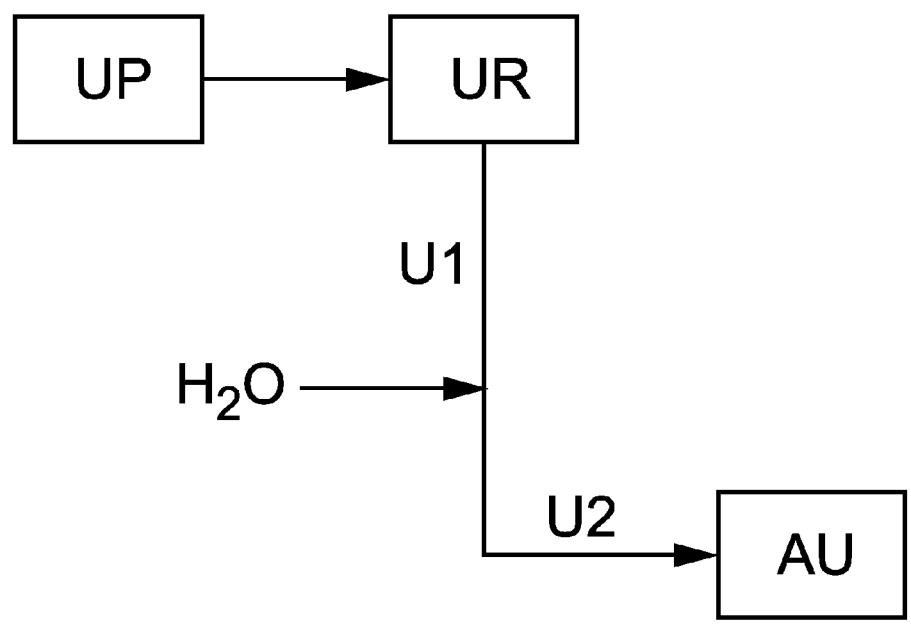
FIG. 2 schematically depicts another embodiment of a urea production process especially developed for the production of a urea-comprising aqueous stream, that is suitable for use in a unit for the reduction of $NO_x$ in combustion engine exhaust gases.

FIG. 2 schematically depicts another embodiment of a urea production process especially developed for the production of a urea-comprising aqueous stream, that is suitable for use in a unit for the reduction of $NO_x$ in combustion engine exhaust gases. This urea production process comprises a urea synthesis section (UP), a urea recovery section (UR), comprising a dissociation unit wherein dissociation is promoted by the addition of $CO_2$ as a stripping agent. A urea-comprising aqueous stream (U1) with a urea content of 79 wt % is separated after this dissociation unit in the urea recovery section and is diluted with water to a urea content of 31.5 wt % to form a diluted urea-comprising aqueous stream (U2). This diluted urea-comprising aqueous stream (U2), having an alkalinity (as $NH_3$) of 0.1% and a carbonate content (as $CO_2$) of 0.05% is stored as a urea-comprising aqueous stream (AU), that is suitable for use in a unit for the reduction of $NO_x$ in combustion engine exhaust gases.

The invention claimed is:

1. A process for the preparation of a urea-comprising aqueous stream that is suitable for use in a unit for the reduction of $NO_x$ in combustion engine exhaust gases according to DIN V70070, wherein the process comprises:
   (a) forming an aqueous urea-comprising process stream at a synthesis pressure in a urea synthesis section of a urea production plant;
   (b) passing the aqueous urea-comprising process stream to at least one recovery section of the urea production plant and subjecting the aqueous urea-comprising process stream in the at least one recovery section to a recovery pressure which is reduced as compared to the synthesis pressure in the urea synthesis section so as to cause dissociation of ammonium carbamate in the aqueous urea-comprising process stream to free ammonia and carbon dioxide;
   (c) removing the free ammonia and carbon dioxide as gas from the aqueous urea-comprising process stream to form a primary urea product stream of the urea production plant;
   (d) separating a first urea-comprising aqueous stream from the aqueous urea-comprising process stream directly after the at least one recovery section in the urea production plant at a point upstream of any evaporation or crystallization section in the urea production plant, and thereafter
   (e) diluting the separated first urea-comprising aqueous stream with water to obtain a second urea-comprising stream which comprises an amount between 31.8-33.2 wt. % of urea and which further has a content of alkalinity as $NH_3$ of max. 0.2% w/w, of biuret of max. 0.3% w/w, of aldehydes of max. 5 mg/kg, of insolubles of max 20 mg/kg, of phosphate of max. 0.5 mg/kg, of copper of max. 0.2 mg/kg, of zinc of max. 0.2 mg/kg, of chromium of max. 0.2 mg/kg, of nickel of max. 0.2 mg/kg, of aluminum of max. 0.5 mg/kg, of magnesium of max. 0.5 mg/kg, of sodium of max 0.5 mg/kg and of potassium of max. 0.5 mg/kg according to the quality requirements for reduction of $NO_x$ in combustion engine exhaust gases according to DIN V70070; and (f) removing the second urea-comprising stream from the urea production plant as an aqueous secondary urea product stream suitable for use in a unit for the reduction of $NO_x$ in combustion engine exhaust gases.

2. The process according to claim 1, wherein the at least one recovery section comprises a dissociation unit in which dissociation is promoted by the addition of a stripping medium, and wherein step (d) of the process comprises separating the first urea-comprising aqueous stream after the dissociation unit.

3. The process according to claim 2, further comprising performing the dissociation by steam stripping at a pressure of 0.001-0.2 MPa.

4. The process according to claim 1, wherein the urea production plant comprises a urea storage tank after the at least one recovery section and, when a shaping section is present, before the shaping section, and wherein step (d) of the process further comprises separating the first urea-comprising aqueous stream from the urea storage tank.

5. The process according to claim 1, wherein the first urea-comprising aqueous stream comprises 60-90 wt % urea.

6. The process according to claim 1, further comprising subjecting the first urea-comprising aqueous stream to dissociation before or after dilution with water.

7. The process according to claim 1, wherein the urea production plant comprises an evaporation section after the at least one recovery section, and wherein step (d) of the process comprises separating the first urea-comprising aqueous stream after the at least one recovery section and before the evaporation section in the urea production plant.

8. The process according to claim 1, wherein the process further comprises a step of concentrating and shaping the primary urea product stream to form a solid urea product, and wherein step (d) of the process comprises separating the first urea-comprising aqueous stream after the at least one recovery section and prior to the step of concentrating and shaping the primary urea product stream.

* * * * *